United States Patent
Feng et al.

(10) Patent No.: US 6,946,583 B2
(45) Date of Patent: Sep. 20, 2005

(54) REFORMING PROCESS FOR MANUFACTURE OF PARA-XYLENE

(75) Inventors: Xiaobing Feng, Houston, TX (US); Thomas H. Colle, Houston, TX (US); Gary D. Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/654,731

(22) Filed: Sep. 4, 2003

(65) Prior Publication Data

US 2004/0044261 A1 Mar. 4, 2004

Related U.S. Application Data

(63) Continuation of application No. 09/882,914, filed on Jun. 15, 2001, now Pat. No. 6,653,518.

(51) Int. Cl.⁷ .................................................. C07C 5/22
(52) U.S. Cl. ...................................... 585/418; 585/419
(58) Field of Search .................................. 585/418, 419

(56) References Cited

U.S. PATENT DOCUMENTS

| | | | |
|---|---|---|---|
| 4,104,320 A | 8/1978 | Bernard et al. | 260/673.5 |
| 4,416,806 A | 11/1983 | Bernard et al. | 502/74 |
| 4,456,527 A * | 6/1984 | Buss et al. | 208/89 |
| 4,721,694 A | 1/1988 | Buss et al. | 502/66 |
| 5,609,751 A | 3/1997 | Wall | 208/133 |
| 6,096,936 A | 8/2000 | Fukunaga et al. | 585/419 |
| 6,177,601 B1 | 1/2001 | Bogdan et al. | 585/419 |

FOREIGN PATENT DOCUMENTS

EP        0 420 100 A1    4/1991    ............ C07C/5/41

* cited by examiner

*Primary Examiner*—Thuan Dinh Dang

(57) ABSTRACT

A process for selectively producing para-xylene from a feedstock enriched in $C_8$ isoalkanes and/or isoalkenes is disclosed. The feed is contacted with Group VIII metal loaded molecular sieve catalyst of low acidity under dehydrocyclization conditions wherein the molecular sieve has a channel size ranging from about 5–8 Angstroms and a 10 to 12 membered ring structure containing at least two elements selected from the group consisting of Si, Al, P, Ge, Ga and Ti.

13 Claims, No Drawings

REFORMING PROCESS FOR MANUFACTURE OF PARA-XYLENE

CROSS-REFERENCE TO RELATED APPLICATIONS

This application is a continuation of U.S. application Ser. No. 09/882,914, filed Jun. 15, 2001, now U.S. Pat. No. 6,653,518 which is hereby incorporated by reference.

BACKGROUND OF THE INVENTION

1. Field of the Invention

This invention relates to a dehydrocyclization process for converting $C_8$ isoalkanes and $C_8$ isoalkenes to para-xylene.

2. Prior Art

Para-xylene (PX) is a valuable basic chemicals useful in chemical industry. Commercial xylenes generally comprise three aromatic isomers, inclusive of PX, and may be produced by reforming hydrocarbon feedstocks rich in naphthenes or by dehydrocyclization of naphtha feedstocks, which are rich in C6 to C20 paraffins, or olefins.

For example, U.S. Pat. No. 3,449,461 discloses the production of mixed xylenes and other aromatics by subjecting a paraffinic feed to dehydrocyclization conditions over a sulfided refractory oxide catalyst containing a noble metal such as platinum. In accordance with U.S. Pat. No. 3,766,291, feedstock comprising 3-methylbutene-1 is converted to PX by disproportionation to 2,5-dimethylhexene which is subsequently dehydrocyclized over a catalyst containing at least one Group VIII metal associated with tin in combination with a Group II aluminate spinel support material.

U.S. Pat. No. 3,428,702 discloses the dehydrocyclization of 2,5-dimethylhexene in the presence of $H_2S$ using a chromia-alumina catalyst such that 30–40% of the 2,5-dimethylhexene is converted to PX. Other dehydrocyclization processes for converting aliphatic or olefinic hydrocarbons to xylenes are found in U.S. Pat. No. 3,207,801, wherein catalysts based on magnesium oxide, hydoxide or magnesium acid salts are used, and in U.S. Pat. No. 4,910,357 wherein a platinum-loaded, non-acidic, metal modified zeolite support such as ZSM-5 is used.

While these and other methods for the production of xylenes are effective and useful, there is a continuing need in the art to provide a process which is highly selective for producing PX and in high yields from hydrocarbon feedstocks containing less valuable alkane and alkene compounds.

SUMMARY OF THE INVENTION

The invention provides a process for producing para-xylene from a feedstock enriched in $C_8$ isoalkane or isoalkene components comprising contacting said feedstock with a dehydrocyclization catalyst under dehydrocyclization conditions of temperature and hydrogen partial pressure, said catalyst comprising a low acidity molecular sieve support having a channel size in the range of about 5–8 angstroms and having a 10 to 12 membered ring structure containing at least two elements selected from the group consisting of Si, Al, P, Ge, Ga and Ti, said molecular sieve further containing at least one Periodic Table Group VIII metal, and recovering a reformate rich in para-xylene.

The process of the invention provides a technique for high conversion of $C_8$ isoalkanes and isoalkenes to xylenes wherein the selectivity ratio of para-xylene to total xylenes present in the reformate is preferably at least about 50 wt %, more preferably at least about 75 wt %.

DETAILED DESCRIPTION OF THE INVENTION

Hydrocarbon feedstocks, which may be dehydrocyclized in accordance with this invention, include naphtha and paraffinic feedstocks, which are enriched in $C_8$ isosikanes or isoalkenes. Such feedstocks may generally comprise a mixture of $C_4$ to $C_{20}$ paraffins and/or alkenes, more preferably $C_8$ to $C_{10}$ paraffins and/or alkenes, In accordance with this invention, the feedstock is enriched in one or a mixture of $C_8$ isoalkanes or isoalkenes, i.e., the feedstock contains greater than 3 wt %, more preferably at least 10 wt %, even more preferably at least 50 wt % and most preferably greater than 90 wt % of said $C_8$ isoalkanes or isoalkenes.

The $C_8$ isoalkane present in the feedstock comprises 2,5-dimethylhexane and the $C_8$ isoalkenes may comprise 2,5-dimethylhexene (2,5-dimethyl-1-hexene, 2,5-dimethyl-2-hexene, 2,5-dimethyl-3-hexene), 2,5-dimethylhexadiene (2,4-, 1,5- and/or 1,3-hexadienes) and 2,5-dimethylhexatriene, including dimers of isobutene.

The dehydrocyclization catalyst used in the present invention comprises a molecular sieve support of low acidity containing at least one Group VIII dehydrogenation metal.

Suitable molecular sieve supports are those having a channel size in the range of about 5 to 8 Angstrons and having a 10 to 12 membered ring structure, such as disclosed in "Atlas of Zeolite Structure Types". W. H. Mejer. D. H. Olson, C. H. Baerlocher, Elsevicr, 4th Edition, 1996, the disclosure of which is incorporated herein by reference. These supports contain at least two elements selected from the group consisting of Si, Al, P, Ge, Ga and Ti, most preferably selected from Si, Al and Ti. Exemplary molecular sieves include zeolite L, *_BEA, ETS-10, ETAS-10, MFI and MTW.

Suitable such supports include the twelve membered ring alkali metal-containing zeolite L aluminosilicates having the general structure:

$$(0.9–1.3)M_{2/n}O:AL_2O_3:XSiO_2:YH_2O$$

wherein M designates at least one exchangeable alkali metal cation, n designates the valance of M, Y may be any value from 0 to about 9 and x is any value between 5 and 7. Preferably M is potassium. These zeolite L materials and their method of manufacture are more completely described in U.S. Pat. Nos. 4,987,109, 5,849,967 and 5,855,863, the complete disclosures of which patents are incorporated herein by reference.

Other suitable molecular sieve supports include the molecular sieves containing at least one octahedral site and tetrahedral sites of at least one type, such as ETS-10 and ETAS-10. The ETS-10 materials are characterized by the unit empirical formula of $$1.0\pm0.25\ M_{2/n}O:TiO_2:ySiO_2:zH_2O$$

wherein M is at least one cation having a valence of n, y is from 2.5 to 25, and z is from 0 to 100. In a preferred embodiment, M is a mixture of alkali metal cations, particularly sodium and potassium, and y is at least 3.5 and ranges up to about 10.

Titanium silicates of this type are more completely disclosed in U.S. Pat. No. 4,853,202, the complete disclosure of which reference is incorporated herein by reference.

Supports of the ETAS-10 type are generally described by the unit empirical formula of:

$$(1+x/2)(1.0\pm0.25\ M_{2/n}O):\ TiO_2:\ xAlO_2:\ ySiO_2:\ zH_2O$$

wherein M is at least one cation having a valence of n, y is from 2 to 100, x is from 0.05 to 5.0 and z is from 0 to 100. In a preferred embodiment, M is a mixture of alkali metal cations, particularly sodium and potassium, and y is at least 2 and ranges up to about 10. Metalloaluminosilicate molecular sieves of this type are more specifically disclosed in U.S. Pat. No. 5,244,650, the complete disclosure of which patent is incorporated hereby by reference.

The molecular sieve support should be of low acidity to minimize isomerization of the para-xylene produced during the dehydrocyclization reaction. Acid sites present in the molecular sieve can be removed by washing the molecular sieve to raise the pH to at least 7, preferably at least 9, as described in U.S. Pat. No. 4,987,109 or by exchanging acid sites on the surface with a cation such as zinc, tin, thallium, lead or alkali or alkaline earth metals. Acid sites can also be blocked by treating the molecular sieve with organosilicon compounds followed by calcination as is known in the art, and by other methods known to those skilled in the art.

In the preferred embodiment, the molecular sieve is sufficiently non-acidic such that it exhibits an alpha value of less than 10, more preferably less than 1, most preferably less than 0.1. The alpha value is a measure of acidity and the test procedure is described in U.S. Pat. No. 3,354,078 as well as in Journal of Catalysis, 4527 (1965), 6278 (1966) and 61,395 (1980), each of which references are incorporated herein by reference.

Because the molecular sieve supports are of micron or submicron size, they are difficult to contain in a fixed bed reactor and would introduce extremely high-pressure drops. The crystals are preferably formed into aggregates such as extrudates, tablets, pills or spherical forms by mixing the crystals with a suitable binder such as alumina, silica or kaolin and water to form a paste, and extruding or otherwise shaping, and cutting the extrudate to form aggregates having a typical dimension of about 1/32 to 1/4 inch. Typical binder content may range from about 10–50 wt % of the final aggregate.

Binderless aggregates of Zeolite L of the type disclosed in U.S. Pat. No. 5,849,967 may also be used in the process.

The molecular sieve serves as a support for at least one Group VIII catalytically active metal to form the dehydrocyclization catalyst. The metal can be loaded onto the support by ion-exchange, impregnation or direct synthesis during the manufacture of the molecular sieve. These metals are typically Group VIII metals which include platinum, rhenium and iridium. Other metals can be added to promote the activity and stability of the catalyst. These include tin, iron, germanium and tungsten. Platinum can be introduced by impregnating the crystals either prior to forming the aggregates or the formed aggregate particles with an aqueous solution of a platinum salt or complex such as chloroplatinous acid, hexachloroplatinic acid, dinitrodiaminoplatinum or platinum tetraamine dichloride. Alternatively, platinum can be introduced by ion exchange with ions in the molecular sieve, using a salt such as platinum tetraamine dichloride. Similar compounds can be used to introduce other metals such as rhenium and iridium into the catalyst. Superior catalysts are obtained when at least 90% of the metals added to the catalyst prior to reduction are less than 7 angstrom in size.

The amount of Group VIII metal incorporated in the molecular sieve support can range from about 0.1 to 10 wt % of the molecular sieve, more preferably from about 0.5 to 2 wt %.

The dehydrocyclization process may be carried out in any suitable fixed bed reactor or other reactor used in reforming processes by passing the $C_8$ enriched feedstream through a bed of the catalyst. For the conversion of naphtha (e.g., C6–C10) and similar mixtures to highly aromatic mixtures, normal and slightly branched chained hydrocarbons, preferably having a boiling range above 40° C. and less than about 200° C., can be converted to products having a substantial higher octane aromatics content by contacting the hydrocarbon feed with the catalyst at a temperature in the range of 400° C. to 600° C., preferably 480° C. to 550° C. at pressure ranging from atomspheric to 40 bar, and liquid hourly space velocities (LHSV) ranging from 0.1 to 15. Hydrogen gas is also introduced, preferably at a ratio of H2/HC of about 1 to 10.

The following examples are illustrative of the invention.

EXAMPLE 1

A Pt/KL catalyst bound with alumina was prepared by the method described in U.S. Pat. No. 4,987,109. The catalyst was tested for 2,5-dimethylhexane cyclodehydrogenation to para-xylene. 50 mg of 60–80 mesh of the above catalyst was packed in a pack-bed reactor. The catalyst was pretreated with a $H_2$ flow of GHSV of 1.7 h$^{-1}$ at 500C and 25 psig for two hours. After pretreatment, a feed containing 2,5-dimethylhexane plus hydrogen at a ratio of $H_2$/HC=4.77 was downflowed through the catalyst bed at a WHSV=1.96 h$^{-1}$ at 25 psig and different temperatures ranging from about 300–475° C. The effluent was analyzed by gas chromatograph to determine the conversion of 2,5-dimethylhexane and selectivity of para-xylene, ethylbenzene, meta-xylene, ortho-xylene and lights using a Chrompack CP-Chirasil DEX CB column. The results are shown in Table 1.

EXAMPLE 2

A Pt/ETAS-10 catalyst was evaluated by the same method as the Pt/KL catalyst in the above example. The catalyst was tested for 2,5-dimethylhexane cyclodehydrogenation to para-xylene reaction under same condition as described in EXAMPLE 1. The results are shown in Table 1.

EXAMPLE 3

Control

A KK-120 commercial reforming catalyst obtained from Criterion was tested for 2,5-dimethylhexane cyclodehydrogenation to para-xylene reaction under same condition as described in Example 1. The products have pX/X of about 38.7%, as shown in Table 1.

TABLE 1

| | Ex. #1 | Ex. #2 | Ex. #3 |
| KX-120 | Pt/KL | Pt/ETAS-10 | |
|---|---|---|---|
| Lights (C1–C4) (wt %) | 1.24 | 6.73 | 15.17 |
| Benzene (wt. %) | 1.65 | 2.57 | 0.25 |
| Toluene (wt %) | 16.22 | 15.77 | 2.04 |
| Para-xylene (wt. %) | 59.70 | 43.92 | 8.4 |
| Meta-xylene (wt. %) | 11.05 | 8.02 | 8.11 |
| Ethylbenzene (wt. %) | 1.48 | 1.61 | 1.29 |
| Ortho-xylene (wt. %) | 2.45 | 2.28 | 5.22 |
| 2,5-DMH conversion (wt. %) | 93.81 | 80.90 | 43.39 |
| PX/X (%) | 81.57 | 80.99 | 38.66 |
| PX/A8s (%) | 79.93 | 78.66 | 36.49 |
| (EB + OX)/A8s (%) | 5.27 | 6.97 | 28.28 |

Table 1 lists the % conversion of 2,5-DMH at 400° C. and the selectivity towards PX vs. total xylenes produced. The catalysts of the invention provide high conversion of 2,5-

DMH and high selectivity towards the production of PX based on total xylenes produced compared to the control EXAMPLE 3.

What is claimed is:

1. A process for producing para-xylene from a feedstock containing at least 5 wt % of $C_8$ isoalkane or isoalkene components comprising:

contacting said feedstock with a dehydrocyclization catalyst under dehydrocyclization conditions of temperature and hydrogen partial pressure to convert $C_8$ isoalkane or isoalkene components into para-xylene said catalyst comprising a A group VIII metal-loaded ETAS-10; and recovering a reformate containing para-xylene having a ratio of para-xylene to the total xylenes present in said reformate of at least about 50%.

2. The process of claim 1 wherein said $C_8$ components are selected from the group consisting of 2,5-dimethylhexane, 2,5-dinuethylliexene, 2,5-dimethylhexadiene, 2,5-dimethylhexatriene and mixtures thereof.

3. The process of claim 1 wherein said group VIII metal is platinum.

4. The process of claim 1 wherein said feedstock contains at least 10 wt % of said $C_8$ components.

5. The process of claim 4 wherein said feedstock contains at least 50 wt % of said $C_8$ components.

6. The process of claim 5 wherein said feedstock contains greater than 90 wt % of said $C_8$ components.

7. The process of claim 1 wherein said ETAS-10 has a alpha value of less than 10.

8. The process of claim 7 wherein said alpha value is less than 1.

9. The process of claim 8 wherein said alpha value is less than 0.1.

10. The process of claim 1 wherein said ratio is at least about 75%.

11. A process for producing para-xylene from a feedstock containing a hydrocarbon mixture containing at least about 5 wt % of $C_8$ isoalkane or isoalkene components comprising:

contacting said feedstock with a dehydrocyclization catalyst under dehydrocyclization conditions of temperature and hydrogen partial pressure to convert $C_8$ isoalkane or isoalkene components into para-xylene, said $C_8$ isoalkane or isoalkene components being selected from 2,5-dimethylhexane, 2,5-dimethylhexene, 2,5-dimethylhexadiene, 2,5-dimethylhexatriene or mixtures thereof; and recovering a reformate containing para-xylene having a ratio of para-xylene to the total xylenes present in said reformate of at least about 50%, wherein said catalyst comprises a A Group VIII metal-loaded ETAS-10.

12. The process of claim 11, wherein the Group VIII metal is one of platinum, rhenium or iridium.

13. The process of claim 12, wherein the molecular sieve further contains a promoter selected from tin, iron, germanium or tungsten.

* * * * *